(12) United States Patent
Liu et al.

(10) Patent No.: US 8,574,614 B2
(45) Date of Patent: Nov. 5, 2013

(54) SURGICAL GRAFTS FOR REPAIRING CHONDRAL DEFECTS

(76) Inventors: Hwa-Chang Liu, Taipei (TW); Feng-Huei Lin, Taipei (TW); Shing-Mou Lee, Taipei (TW); Chun-Che Yen, Taichung (TW)

( * ) Notice: Subject to any disclaimer, the term of this patent is extended or adjusted under 35 U.S.C. 154(b) by 116 days.

(21) Appl. No.: 12/700,469

(22) Filed: Feb. 4, 2010

(65) Prior Publication Data
US 2011/0189254 A1 Aug. 4, 2011

(51) Int. Cl.
*A61F 2/00* (2006.01)
*A01N 63/00* (2006.01)
*A01N 65/00* (2009.01)

(52) U.S. Cl.
USPC .................... 424/423; 424/93.1; 424/93.7

(58) Field of Classification Search
USPC .................................. 623/23.63, 23.72
See application file for complete search history.

(56) References Cited

U.S. PATENT DOCUMENTS

| 7,459,307 | B2 | 12/2008 | Ha | |
|---|---|---|---|---|
| 2001/0005592 | A1* | 6/2001 | Bhatnagar et al. | 435/395 |
| 2003/0050709 | A1* | 3/2003 | Noth et al. | 623/23.58 |
| 2004/0258731 | A1* | 12/2004 | Shimoboji et al. | 424/426 |

FOREIGN PATENT DOCUMENTS

EP 1760144 3/2005

OTHER PUBLICATIONS

Bosnakovski et al. Biotechnol Bioeng. Apr. 20, 2006;93(6):1152-63.*
Pound et al. Biomaterials, vol. 28, Issue 18, 2007, pp. 2839-2849.*
Chang, et al., "Thoughts and Progress", Artificial Organs, 561-571, vol. 32, No. 7, 2008.
Hui et al., "In Vitro Chondrogenic Differentiation of Human Mesenchymal Stem Cells in Collagen Microspheres: Influence of Cell Seeding Density and Collagen Concentration," Biomaterials 29 (2008) 3201-3212.

* cited by examiner

*Primary Examiner* — Janet Epps-Smith

(57) ABSTRACT

An implant containing a collagen matrix embedded with chondrocyte-like cells, its use in repairing a chondral defect, and a method of preparing the implant.

17 Claims, 2 Drawing Sheets

SURGICAL GRAFTS FOR REPAIRING CHONDRAL DEFECTS

FIELD OF THE INVENTION

The preset invention relates to surgical grafts for repairing a chondral defect.

BACKGROUND OF THE INVENTION

Autogenous chondrocyte transplantation has been used to treat the chondral defect since 1994, comprising collecting chondrocytes from normal cartilage tissues, expanding these cells in a medium in vitro as much as possible, and then filling the chondral defect by implanting the expanded cells in artificial scaffolds. However, there are still many problems; for example, the source of autogenous chrondrocytes is limited, the proliferation ability of chondrocytes is low, and their unique phenotypes may be lost during expansion (Saadeh et al., Human cartilage engineering: chondrocyte extraction, proliferation, and characterization for construct development. Ann Plast Surg 1999; 42:509-13).

Mesenchymal stem cells (MSCs) are able to differentiate into cells of connective tissue lineages including cartilage and thus becomes an attractive cell source for cartilage tissue engineering. Many methods have been used in chondrogenic induction of MSCs. Kavalkovich et al. provided a pellet culture method mimicking the environment of embryonic cartilage development, wherein a high cell density of cells were obtained but a tightly aggregated cell mass with a large amount of cells forming only a small volume of chondral tissue was present. Therefore, a considerably large number of the cell pellets were required for repairing a defective cartilage, and the large pellets exhibited a periphery of viable cells, but the pellet center became necrotic (Kavalkovich et al., Chondrogenic differentiation of human mesenchymal stem cells within an alginate layer culture system. In Vitro Cell Dev Biol Anim 2002; 38:457-66.). In addition, pellets are difficult to handle and to mold into various shapes needed for defect repair. Given the above, the pellet culture is impractical for surgical applications. Furthermore, it was found that embedding human MSCs (hMSCs) in agarose or alginate gels could be cast into various shapes and caused substantial chondrogenesis (Huang et al., Chondrogenesis of human bone marrow-derived mesenchymal stem cells in agarose culture. Anat Rec A Discov Mol Cell Evol Biol 2004; 278:428-36; and Ma et al., Chondrogenesis of human mesenchymal stem cells encapsulated in alginate beads. J Biomed Mater Res A 2003; 64:273-81). However, the alginate or agarose scaffolds for cartilage tissue engineering have the drawbacks: poor cell adhesion, and uncontrollable degradation of alginate following the diffusion of divalent cations into the surrounding medium. In addition, alginate matrices were used in the in vivo applications and reported to have severe foreign body giant cell reactions and immunological responses when implanted to treat full-thickness defects in cartilage in experimental animals (Hunziker, Articular cartilage repair: basic science and clinical progress. A review of the current status and prospects. Osteoarthritis Cartilage 2001; 0:432-63). Hence, alginate matrices have not been employed in human patients for articular cartilage repair.

Therefore, it is still desired to develop a surgical graft for repairing a chondral defect in a patient.

SUMMARY OF THE INVENTION

The present invention is based on two unexpected discoveries that (1) an implant containing a collagen matrix embedded with chondrocyte-like cells repairs chondral defects when implanted at a chondral defect site, and (2) no gap forms between the implant and the tissues at the implanting site.

Accordingly, one aspect of this invention features a chondral defect-repairing implant that contains a collagen matrix embedded with chondrocyte-like cells and supplemented with transforming growth factor beta one (TGF-β1). This implant, free of lacunae, is prepared by cultivating mesenchymal stem cells (MSCs) in a collagen (e.g., type-I or type-II collagen) containing medium supplemented with TGF-β1 under conditions allowing differentiation of MSCs to the chondrocyte-like cells and formation of the implant. The chondrocyte-like cells secret glycosaminoglycan. The MSCs can be obtained from bone marrow, adipose tissue, muscle tissue, dental pulp of deciduous baby teeth, umbilical cord blood, Wharton's jelly, placenta, or cord lining membrane.

In example, the cultivating step mentioned above is performed by culturing the MSCs in a collagen containing medium supplemented with TGF-β1 for 7 to 21 days under conditions allowing formation of a collagen matrix and differentiation of the MSCs into chondrocyte-like cells, which are embedded in the collagen matrix. The collagen containing medium preferably has a collagen concentration of about 1-about 10% w/v (e.g., about 3% w/v). This cultivating step can be carried out in a capsule.

Another aspect of this invention features a method of repairing a chondral defect by placing the implant described above in a subject in need of the treatment at a chondral defect site. In one example, the implant is delivered to the defect site with a syringe-like piston. In another example, the implant, loaded in a capsule, is delivered to the defect site by squeezing it out of the capsule and applying it to the site.

The various embodiments of the present invention are described in details below. Other characteristics of the present invention will be clearly presented by the following detailed descriptions and drawings about the various embodiments and claims.

BRIEF DESCRIPTION OF THE DRAWINGS

For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Figure 1:
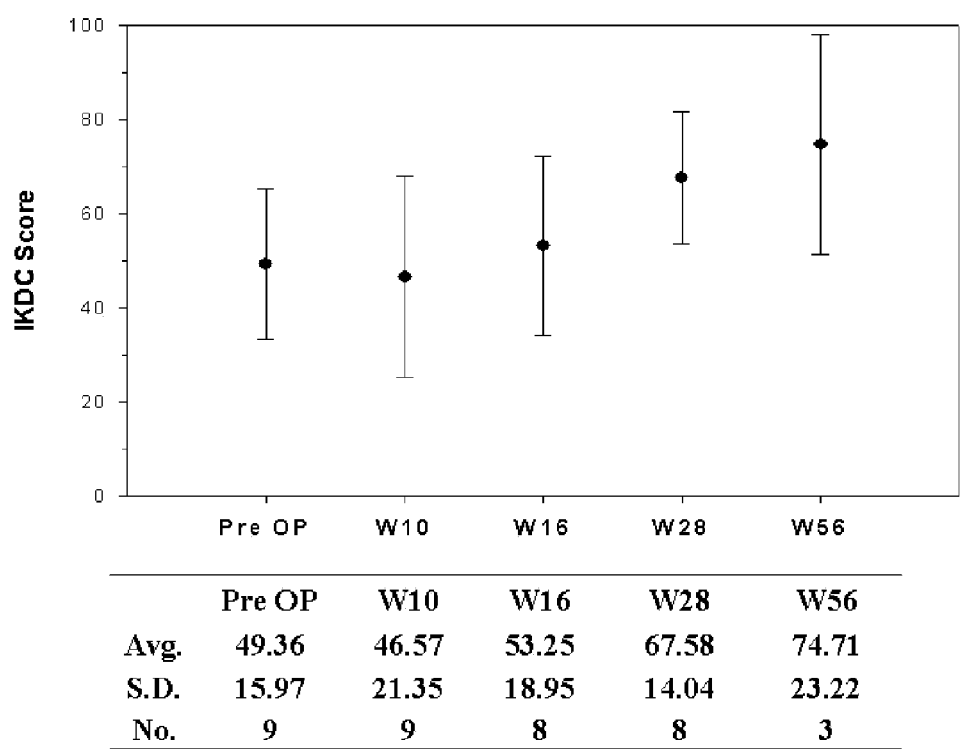
FIG. 1 shows the IKDC scoring of the 9 patients treated with the method according to the invention, wherein a significant improvement by Student's t-test was found 6 months and 12 months after operation.

The present invention features a method for repairing a chondral defect in a patient with an implant comprising a collagen matrix embedded with chondrocyte-like cells and transforming growth factor beta one (TGF-β1) wherein the chondrocyte-like cells being differentiated from mesenchymal stem cells (MSCs) and secreting glycosaminoglycan, whereby the chondral defect can be repaired without any gap between the graft.

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "mesenchymal stem cells" or "MSCs" used herein refers to multipotent stem cells derived from adult tissues including but not limited to bone marrow, adipose tissue, muscle tissue, dental pulp of deciduous baby teeth, umbilical cord blood, or Wharton's jelly.

As used herein, the term "chondrocytes" refers to mature cartilage cells, which are embedded within the lacunae (small cavities) in the matrix. Chondrocytes arise by differentiation of mesenchymal chondrogenic cells into chondroblasts, which are the earliest cells to produce cartilage matrix. Mature chondrocytes are large secretory cells with a spherical nucleus and a prominent nucleolus. Therefore, the formation of lacuna in chondrocytes is regarded as a mature chondrocyte character.

As used herein, the term "chondrocyte-like cells" refers to the cells that possess the properties of the chondrocyte secretory cells, such as secreting glycosaminoglycan (GAG), but do not form lacunae, a typical character of mature chondrocytes.

As used herein, the term "a collagen matrix" refers to a tissue-engineered product formed by culturing the MSCs in a collagen containing medium, which is embedded with chondrocyte-like cells that are capable of secreting glycosaminoglycan (GAG) but without lacunae.

The present invention provides A method for repairing a chondral defect in a patient comprising:

providing an implant containing a collagen matrix embedded with chondrocyte-like cells and transforming growth factor beta one (TGF-β1), the chondrocyte-like cells being differentiated from mesenchymal stem cells (MSCs) and secreting glycosaminoglycan, and placing the implant in the patient at a chondral defect site; wherein the implant is free of lacunae.

In the invention, the implant containing a collagen matrix embedded with chondrocyte-like cells and transforming growth factor beta one (TGF-β1), which may be obtained by cultivating MSCs in a collagen containing medium supplemented with transforming growth factor beta one (TGF-β1) under conditions allowing differentiation of the MSCs to the chondrocyte-like cells and formation of the implant.

In one example of the invention, the MSCs were cultivated in a collagen (e.g., type-I or Type-II collagen) containing medium supplemented with TGF-β1 for differentiation from the MSCs to chondrocyte-like cells that were characterized by evaluating the glycosaminoglycan (GAG) content to ensure that the MSCs were induced to cartilage-like tissue, and detecting whether lacunae was formed. The collagen matrix embedded with chondrocyte-like cells were collected; which is a tissue-engineered construct used as an implant.

In one example of the invention, the MSCs were expanded, and cultured, and then embedded and cultured in a medium containing collagen, and supplemented with transforming growth factor beta one (TGF-β1) under conditions for chondrogenic induction into chondrocyte-like cells. The collagen matrix embedded with chondrocyte-like cells that secrete glycosaminoglycan (GAG) is collected. The collagen matrix can be examined via routine methods to confirm that no lacunae formation occurs and that the chondrocyte-like cells embedded therein secret GAG.

In the invention, any standard methods, conditions or technology may be used to allow the MSCs to differentiate to the chondrocyte-like cells and formation of the collagen matrix as an implant.

In one example of the invention, collagen may be type-I or type-II collagen, or combination thereof. The concentration of collagen may be about 1%—about 10% collagen, preferably about 3%.

According to the invention, the implant may be easily delivered to a chondral defect site by a syringe-like piston. In one embodiment of the invention, the implant is loaded in a capsule and the implant may be placed by squeezing the implant out of the capsule and applying it to the chondral defect site.

Accordingly, the invention also provides an implant for repairing a chondral defect, comprising a collagen matrix embedded with chondrocyte-like cells and supplemented with transforming growth factor beta one (TGF-β1), the chondrocyte-like cells being differentiated from mesenchymal stem cells (MSCs) and secreting glycosaminoglycan, wherein the implant is free of lacunae.

According to the invention, the implant may be prepared by the method comprising:

providing mesenchymal stem cells (MSCs); and cultivating the MSCs in a conllagen containing medium supplemented with transforming growth factor beta one (TGF-β1) under conditions allowing differentiation of the MSCs to the chondrocyte-like cells that and formation of the implant.

The present invention will now be described more specifically with reference to the following embodiments, which are provided for the purpose of demonstration rather than limitation.

Example 1

Isolation and Culture of Human MSCs

Ten (10) ml of heparinized bone marrow blood was aspirated from the ilium of the pelvis, and bone marrow MSCs were isolated therefrom. The MSCs were cultured in Dulbecco's modified Eagle's medium with low glucose containing 10% fetal bovine serum at 37° C. under 5% carbon dioxide and 95% humidity. The medium was changed twice a week. The cells were trypsinized and subcultured at a ratio of 1:3 every week, and then harvested and embedded in Porcogen™ collagen solution (3% type-I/type-III collagen, SunMax Biotech., Taiwan) containing serum-free DMEM-LG only. The cells were cultured at 0.5 mL aliquots with a final cell density of $2.6 \times 10^6$ cells/cm$^2$ to gel in 24-well plates at 37° C. for 1 hour followed by the addition of 2.0 mL medium per well containing: serum-free DMEM-LG containing ITS+ Premix, 50 ug/mL L-ascorbic acid-2-phosphate, $10^{-7}$ M dexamethasone, supplemented with 10 ng/mL TGF-β1 (Pepro Tech; Rocky Hill, N.J.). The cells were cultured in the just-described medium for 7 to 21 days, with the medium being changed every three days, to allow the cells dispersive embedded in the collagen containing medium to obtain a collagen matrix embedded with chondrocyte-like cells. The cell/collagen mixtures were analyzed 7, 14, and 21 days after the cell seeding to ensure if GAG was secreted and the lacunae had not yet formed to obtain the cell-matrix complexes.

Example 2

Characterization of the Cell-Matrix Complex

The cell-matrix complexes were harvested, embedded in paraffin and cut into 5 μm slices. The slices were deparaffinized, and rehydrated by sequential immersion in 100% xylene, 100% ethanol, 70% ethanol, and water. Hematoxylin and eosin staining (Muto, Tokyo, Japan) of sample sections was used to evaluate the cell morphology. In addition, Alcian Blue staining (Sigma) was used to evaluate the glycosaminoglycan (GAG) content.

Example 3

Investigation on Human Patients

1. Patient Populations

Patients with chondral or osteochondral defects from osteochondritis dissecans or osteonecrosis of medial femoral condyle, or limited chondral defects of osteoarthritis which was located on the weight-bearing site were selected. However, patients with immature bone, severely degenerative arthritis in which total joint arthroplasty is needed, other defects such as cruciate ligament rupture and meniscus injury, arthritis such as rheumatoid arthritis and gouty arthritis, and infectious disease such as AIDS and Hepatitis B; patients completely bed-ridden above three months; patients taking corticosteroids longer than two weeks, and alcoholism are excluded. Totally, 10 patients were recruited. Among them, six were female and four were male. The patients' average age was 66 (ranging from 47 to 83).

2. Operation

An anterior midline incision was made on the knee and the articular surface of the medial femoral condyle was exposed using a medial parapatellar approach. The knee flexed extremely to made access to the osteochondral defect easy. The bone defect was debrided and filled with cancellous bone taken from the upper tibia. Then, the cell-matrix complexes as obtained in Example 1 as surgical grafts were transplanted onto the defects. Finally, periosteum taken from the proximal tibia was used to cover the surgical graft. After operation, all patients received regular Quadriceps muscle training and exercise to improve range of motion of the knee.

3. Clinical Assessment

The knee function of all 10 patients was scored by the International Knee Documentation Committee Subjective Knee Form (IKDC) and X-ray examination was done preoperatively and at 1.5, 3, 6 and 12 months of follow-up. Magnetic Resonance Imaging (MRI) was carried out 6 months and 12 months after operation. Arthroscopic examination and biopsy was performed 12 months after operation if patients accept the proposal. Student t-test was used for statistical analysis.

4. Results

Figure 2:
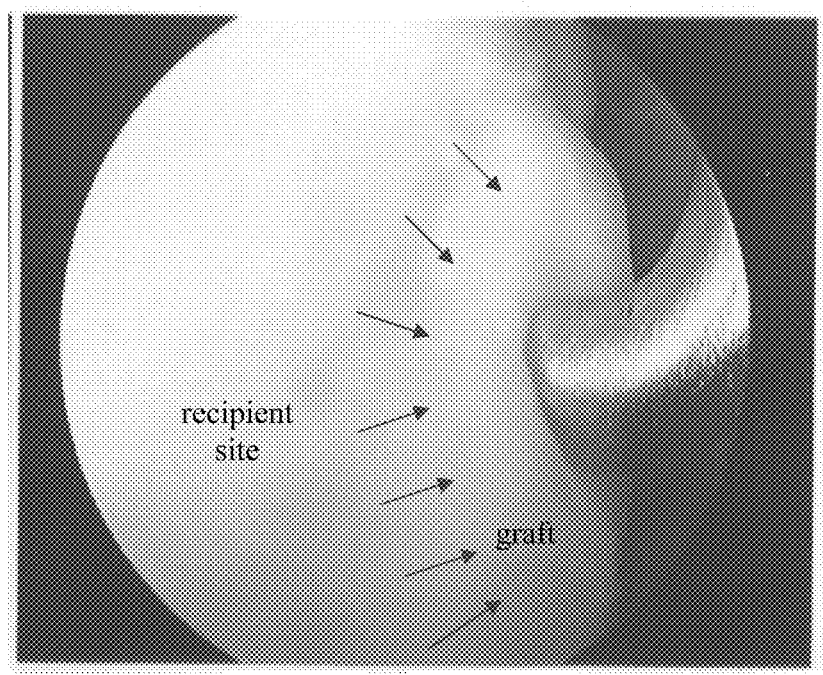
FIG. 2 is an image showing the arthroscopic observation of a patient treated with the method according to the invention 12 months after the transplantation; wherein there was no gap between the recipient site and the surgical graft created by the cell-matrix complex.

Except one patient who did not want to come back for evaluation 6 months after operation, the remained 9 patients were followed up regularly up to 12 months. As shown in FIG. 1, the IKDC scoring of the patients treated with the method according to the invention had significant improvement by Student's t-test was found 6 months and 12 months after operation. All 9 patients felt much better 6 months after operation. Four patients were followed up more than 12 months and 3 of them received arthroscopy. The chondral defects were found in the hyaline cartilage with moderate hardness that were merged without any gap between the recipient site and the graft (see FIG. 2).

Given the above, the cell-matrix complex comprising chondrocyte-like cells secreting GAG but without lacunae and the matrix prepared therefrom according to the invention, exhibited excellent efficacy in repairing a chondral defect in a patient, after transplanting onto the recipient site, where hyaline cartilage was formed without any gap between the recipient site and the surgical graft created by the cell-matrix complex.

We claim:

1. A method for repairing a chondral defect in a patient comprising:
providing an implant containing a collagen matrix embedded with chondrocyte-like cells, the chondrocyte-like cells being differentiated from mesenchymal stem cells (MSCs) and being glycosaminoglycan-secreting, and
placing the implant in the patient at a chondral defect site;
wherein the implant is free of lacunae and is prepared by cultivating the MSCs for 7 to 20 days in a collagen-containing medium supplemented with transforming growth factor beta one (TGF-$\beta$1) under conditions allowing differentiation of the MSCs to the chondrocyte-like cells and formation of the implant.

2. The method of claim 1, wherein the MSCs are isolated from bone marrow, adipose tissue, muscle tissue, dental pulp of deciduous baby teeth, umbilical cord blood, Wharton's jelly, placenta, or cord lining membrane.

3. The method of claim 1, wherein the collagen is contained in the medium at a concentration of about 1% to about 10% w/v.

4. The method of claim 3, wherein the collagen is contained in the medium at a concentration of about 3% w/v.

5. The method of claim 1, wherein the matrix contains type-I or type-II collagen.

6. The method of claim 1, wherein the placing step is performed by delivering the implant to the chondral defect site by a syringe-like piston.

7. The method of claim 1, wherein the implant is loaded in a capsule and the placing step is performed by squeezing the implant out of the capsule and applying it to the chondral defect site.

8. An implant for repairing a chondral defect, comprising a collagen matrix embedded with chondrocyte-like cells, wherein the implant, free of lacunae, is prepared by cultivating mesenchymal stem cells (MSCs) for 7 to 20 days in a collagen-containing medium supplemented with transforming growth factor beta one (TGF-$\beta$1) under conditions allowing differentiation of the MSCs to the chondrocyte-like cells and formation of the implant, the chondrocyte-like cells being glycosaminoglycan-secreting.

9. The implant of claim 8, wherein the MSCs are isolated from bone marrow, adipose tissue, muscle tissue, dental pulp of deciduous baby teeth, umbilical cord blood, Wharton's jelly, placenta, or cord lining membrane.

10. The implant of claim 8, wherein the collagen matrix contains type-I or type-II collagen.

11. A method for preparing the implant of claim 8, comprising:
providing mesenchymal stem cells (MSCs); and
cultivating the MSCs for 7 to 20 days in a collagen-containing medium supplemented with transforming growth factor beta one (TGF-$\beta$1) under conditions allowing differentiation of the MSCs to the chondrocyte-like cells and formation of the implant.

12. The method of claim 11, wherein the MSCs are isolated from bone marrow, adipose tissue, muscle tissue, dental pulp of deciduous baby teeth, umbilical cord blood, Wharton's jelly, placenta, or cord lining membrane.

13. The method of claim 11, wherein the collagen is contained in the medium at a concentration of about 1% to about 10% w/v.

14. The method of claim 13, wherein the collagen is contained in the medium at a concentration of about 3% w/v.

15. The method of claim 11, wherein the matrix contains type-I or type-II collagen.

16. The method of claim 11, further comprising, after the cultivating step, confirming that the chondrocyte-like cells secret glycosaminoglycan and the implant is free of lacunae.

17. The method of claim 11, wherein the cultivating step is performed in a capsule.

\* \* \* \* \*